(12) United States Patent
Wang et al.

(10) Patent No.: US 7,488,584 B2
(45) Date of Patent: Feb. 10, 2009

(54) METHODS FOR DIAGNOSING AND TREATING KIDNEY AND COLORECTAL CANCER

(75) Inventors: Bruce Wang, Mountain View, CA (US); Matthias Wabl, San Francisco, CA (US)

(73) Assignee: Picobella, Burlingame, CA (US)

( * ) Notice: Subject to any disclaimer, the term of this patent is extended or adjusted under 35 U.S.C. 154(b) by 0 days.

(21) Appl. No.: 11/388,550

(22) Filed: Mar. 24, 2006

(65) Prior Publication Data

US 2007/0224600 A1    Sep. 27, 2007

(51) Int. Cl.
*G01N 33/574* (2006.01)
(52) U.S. Cl. ...................... 435/7.23; 435/7.1
(58) Field of Classification Search .................. None
See application file for complete search history.

(56) References Cited

FOREIGN PATENT DOCUMENTS

WO    WO03/047526 A2    6/2003
WO    WO03/047526 A3    6/2003

OTHER PUBLICATIONS

Harlow and Lane (Antibodies, a Laboratory Manual, Cold Spring Harbor Laboratory Press, 1988, Ch. 5, pp. 75-76).*
Montesano, R et al,1996, Intl J Cancer, 69(3): 225-235.*
Similarly, Burmer, GC et al, 1991, Environmental Health perspectives, 93: 27-31.*
Busken, C et al, Digestive Disease Week Abstracts and Itinerary Planner, 2003, abstract No. 850.*
Freshney (Culture of Animal Cells, A Manual of Basic Technique, Alan R. Liss, Inc., 1983, New York, p. 4).*
Buchner and Meisler, *Gene*, 307:23-30 (2003).
Collier et al., *Nature*, 436:272-276 (2005).
Dupuy et al., *Nature*, 436:221-226 (2005).
Lund et al., *Nat Genet*, 32:160-165 (2002).
Mikkers et al., *Nat Genet*, 32:153-159 (2002).
Nusse et al., *Cell*, 31:99-109 (1982).
Nusse et al., *Nature*, 307:131-136 (1984).
Sorensen et al., *J Virol.*, 70:4063-4070 (1996).
International Search report and Written opinion for PCT application PCT/US2007/006876, search report dated Aug. 19, 2008, 8 pages (2008).

* cited by examiner

*Primary Examiner*—Misook Yu
*Assistant Examiner*—Mark Halvorson
(74) *Attorney, Agent, or Firm*—Susan J. Myers Fitch; Peter J. Dehlinger; King & Spalding LLP (57) ABSTRACT

Methods, reagents and kits for diagnosing and treating cancer such as kidney or colorectal cancer are disclosed. An immunoassay for detecting kidney or colorectal cancer is based on the relative change of the ADAMTSL4 protein in urine or blood compared with normal tissue. An immunohistochemical assay for detecting kidney or colorectal cancer is based on the relative absence of labeled antibody binding to cancerous tissue, compared with normal tissue.

10 Claims, 2 Drawing Sheets

METHODS FOR DIAGNOSING AND TREATING KIDNEY AND COLORECTAL CANCER

I. REFERENCES

The following references are cited below in support of the background of the invention or methods employed in practicing the invention.
1. Buchner and Meisler, "TSRC1, a widely expressed gene containing seven thrombospondin type I repeats," *Gene*, 307:23-30 (2003).
2. Nusse, et al., "Mode of proviral activation of a putative mammary oncogene (int-1) on mouse chromosome 15," *Nature*, 307:131-136 (1984).
3. Nusse, et al., "Many tumors induced by the mouse mammary tumor virus contain a provirus integrated in the same region of the host genome," *Cell*, 31:99-109 (1982).
4. Sorensen, et al., "Sequence tags of provirus integration sites in DNAs of tumors induced by the murine retrovirus SL3-3," *J Virol*, 70:4063-4070 (1996).
5. Lund, et al., "Genome-wide retroviral insertional tagging of genes involved in cancer in Cdkn2a-deficient mice," *Nat Genet*, 32:160-165 (2002).
6. Mikkers, et al., "High-throughput retroviral tagging to identify components of specific signaling pathways in cancer," *Nat Genet*, 32:153-159 (2002).
7. Collier, et al., "Cancer gene discovery in solid tumours using transposon-based somatic mutagenesis in the mouse," *Nature*, 436:272-276 (2005).
8. Dupuy, et al., "Mammalian mutagenesis using a highly mobile somatic Sleeping Beauty transposon system," *Nature*, 436:221-226 (2005).

II. BACKGROUND

Cancer is caused by genetic aberrations, i.e., mutations. In mutant cells the normal balance between the factors that promote and restrain growth is disrupted, and as a result, these mutant cells proliferate continuously—the hallmark of tumor cells. Mutations can arise spontaneously or by external factors such as chemical mutagens, radiation, or viral integration, which inserts extra-genomic DNA that may or may not contain an oncogene. A cellular gene can be modified by point mutation, insertion and frame shift (including truncation), (functional) deletion (including silencing), or translocation, which sometimes can result in gene fusion. In this way, proto-oncogenes become oncogenes, which promote proliferation, and tumor suppressor genes become inactivated, also inducing tumor growth. Any combination of the above-mentioned changes in DNA can contribute to tumor formation. There are two ways by which mutations result in transformation: the expression level of the genes is changed, or their function is altered. The consequences of these changes may or may not be held in check by the immune system (immune surveillance).

Heretofore, there has been no demonstrated link between changes in ADAMTSL4 levels and kidney and/or colorectal cancer. Such a link could have a number of important diagnostic and therapeutic applications. It has now been discovered that (i) ADAMTSL4 levels change, e.g. decrease significantly in kidney cancer and colon tumor cells, and (ii) this change can be measured in blood-fluid and urine sample of patients.

III. SUMMARY

In one aspect, a histological method for examining human tissue for the presence and extent of cancer is provided. This method involves the steps of staining the human tissue with an antibody specific against a selected domain or epitope of ADAMTSL4 and labeled with a detectable marker, to attach the marker to the surface of tissue cells having surface bound ADAMTSL4 protein with that epitope or domain, and determining, based on a reduced distribution and extent of detectable marker with respect to the distribution and extent of marker in normal cells, the presence and extent of cancer in the tissue.

In one embodiment, the antibody is specific against an epitope contained within at least one of SEQ ID NO:1 and SEQ ID NO:2. In other embodiments, the antibody may be specific against a thrombospondin repeat. In specific embodiments, the antibody is specific against a thrombospondin repeat selected from the group consisting of SEQ ID NOS:3-9. In another embodiment, the antibody is specific against an ADAM-TS spacer represented by SEQ ID NO:10. In an additional embodiment, the antibody is specific against an epitope contained within the ADAMTSL4 isoform 1 amino acid defined by SEQ ID NO:11 or the ADAMTSL4 isoform 2 amino acid defined by SEQ ID NO:12.

The human tissue may be selected from the group consisting of kidney tissue, colon tissue, and/or rectal tissue.

The antibody may further be labeled with a detectable marker suitable for immunohistochemical detection of cancerous kidney, colorectal, or neuronal tissue, based on the relative absence of histochemical staining of the tissue compared with normal kidney colorectal, or neuronal issue, respectively.

Also disclosed is a method for identifying genetic mutations associated with an increased risk of kidney and/or colorectal cancer. The method involves (a) extracting genomic DNA from cells from cancerous tissue from human patients, (b) for the DNA extracted from cells from each tissue, comparing the sequence of the DNA in a region selected from at least one of (i) a plurality of exons 1 to 17 of the ADAMTSL4 on chromosome 1q21, including adjacent splice site acceptor and donor sequences of the exons, (ii) a 5' UTR region within 10 kB or less of exon 1 of the gene, and (iii) a 3' UTR region within 10 kB or less of exon 17, with a homologous region of DNA from cells from normal, wildtype human tissue, and (c), by said comparing, identifying one or more mutations in said regions associated with an increased risk of kidney or colorectal cancer. In one embodiment, the DNA that is compared is a 5' UTR region within 10 kB or less of exon 1 of the ADAMTSL4 gene.

The method may be used in constructing a gene chip designed for genetic screening for risk of cancer. For each mutation identified in step (c), a gene fragment capable of binding selectively to genomic DNA fragments carrying that mutation, but not to corresponding wildtype DNA fragments is produced, and the different-sequence fragments are attached at known positions on a gene-chip substrate.

In yet another aspect, there is provided a method for screening for kidney or colorectal cancer in a human subject, or staging treatment of kidney or colorectal cancer in a subject by reacting a body-fluid sample from the subject with an antibody specific against a selected domain or epitope of ADAMTSL4, and determining from the presence and/or amount of immunoassay product, whether the subject has a reduced level of ADAMTSL4 protein lacking the specific domain or epitope, when compared with a normal range of ADAMTSL4 in human samples, as an indicator of kidney and/or colorectal cancer. The body-fluid sample may be urine, and the assayed level of ADAMTSL4 indicative or kidney or colorectal cancer may be a level less than about 0.1 ng/ml.

The method may be carried out by applying the body fluid to a solid-phase immunoassay device, the level of ADAMTSL4 in the sample may be indicated qualitatively by a colorimetric or fluorometric indicator, and the determining step may include comparing the indicator with a known standard.

In a related aspect, a diagnostic device for use in for screening for kidney and/or colorectal cancer in a human subject, or staging treatment of kidney and/or colorectal cancer in a subject is provided. The device comprises (a) structure for receiving a body-fluid sample from the subject, (b) an antibody specific against a selected domain or epitope of ADAMTSL4, and associated with the structure and capable of reacting with body-fluid received in the structure, to produce, in combination with other reagents associated with the structure, a detectable reaction indicative of the presence of ADAMTSL4 sample protein containing that epitope or domain, and (c) a known-standard indicator against which the level of detectable reaction produced can be assessed as a reduced level associated with kidney or colorectal cancer.

The structure in the device may include a porous pad having the antibody embedded therein, for reaction with the fluid sample when the sample is applied to the pad, the detectable reaction may be indicated by a colorimetric or fluorometric indicator, and the known standard indicator may include an indicia that represents a level of ADAMTSL4 containing the epitope or domain corresponding to that associated with kidney and/or colorectal cancer.

The device may be employed in a kit which includes a spectrophotometric detector for generating a signal related to the level of ADAMTSL4 produced, a microprocessor for comparing the signal with a known-standard signal value associated with kidney and/or colorectal cancer, and a display for displaying an output of the microprocessor. The anti-ADAMTSL4 binding protein may be specific against an epitope contained within SEQ ID NO:11 and/or SEQ ID NO:12. In another embodiment, the anti-ADAMTSL4 binding protein may be specific against an epitope selected from SEQ ID NO:1 and/or SEQ ID NO:2

Also provided is a method of treating kidney or colorectal cancer in a subject by the steps of (a) reacting a body-fluid sample from the subject with an antibody specific against a selected domain or epitope of ADAMTSL4, (b) determining from the presence and/or amount of immunoassay product, whether the subject has a reduced level of ADAMTSL4 protein lacking the specific domain or epitope, when compared with a normal range of ADAMTSL4 in human samples, as an indicator of kidney and/or colorectal cancer, and (c) if the subject has such a reduced ADAMTSL4 level, administering a therapeutically effective amount of a ADAMTSL4 antibody effective, when bound to the surface of kidney or colorectal cancer cells, to inhibit growth or viability of the cells. One exemplary antibody for use in the method is a human or humanized anti-ADAMTSL4 antibody specific against an epitope contained within SEQ ID NO:11 or SEQ ID NO:22. In a specific embodiment, the anti-ADAMTSL4 antibody is specific against an epitope selected from SEQ ID NO:1 and/or SEQ ID NO:2.

These and other aspects, objects, advantages, and features of the invention will become apparent to those persons skilled in the art upon reading the details of the invention as more fully described below.

IV. BRIEF DESCRIPTION OF THE DRAWINGS

The invention is best understood from the following detailed description when read in conjunction with the accompanying drawings. It is emphasized that, according to common practice, the various features of the drawings are not to-scale. The dimensions of the various features are arbitrarily expanded or reduced for clarity.

V. DETAILED DESCRIPTION

Before the present methods to diagnose and treat kidney and colon and rectal, together colorectal, cancers are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the sequenc" includes reference to one or more sequences and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

A. Definitions

The following terms have the definitions given below, unless otherwise indicated in the specification.

"Screening" for kidney or colorectal cancer, in accordance with the present invention, means testing individuals for a level of ADAMTSL4 that is indicative of kidney and/or colorectal cancer or an elevated risk of kidney and/or colorectal cancer.

"Staging" treatment of kidney or colorectal cancer, in accordance with the present invention, involves determining the stage of kidney and/or colorectal cancer in an individual, based on the level of ADAMTSL4 detected, and tailoring the treatment to that stage. There are four recognized stages of cancer, which are defined by the degree of localization of cancer cells. In addition, kidney cancer may be defined as early stage at which the cancer is responsive to a number of hormonal-based therapies, and a later, more serious androgen-independent stage.

"A reduced level of ADAMTSL4 protein" may include, as an indicator of cancer, a reduced level of wildtype ADAMTSL4 protein or a reduced level of ADAMTSL4 protein having a specific epitope or domain. That is, either the absence of any ADAMTSL4 protein or the presence of a defective ADAMTSL4 protein may be indicative of cancer, e.g., kidney and/or colorectal cancer.

"Colorectal" as used herein refers to colon and/or rectal tissue. "Colorectal cancer" refers to cancer of the colon, rectum, anus, and/or appendix.

B. ADAMTSL4 Protein and Expression

The thrombospondin type 1 repeat domain is found in many proteins with diverse biological functions including cellular adhesion, angiogenesis, and patterning of the developing nervous system. Alternate transcriptional splice variants, encoding different isoforms, have been characterized.

The thrombospondin type 1 repeat containing protein, ADAMTSL4, (previously TSRC1) is a member of the ADAMTS-like gene family (a disintegrin and metalloproteinase with thrombospondin motifs). TSRs are extracellular protein domains that often contain a protein binding site. The thrombospondin type 1 repeat domain is found in many proteins with diverse biological functions including cellular adhesion, angiogenesis, and patterning of the developing nervous system (Buchner and Meisler). The human and the mouse genes encode proteins of 1074 and 1036 amino acid residues (AA), respectively (Buchner et al.). At least two alternatively spliced transcript variants encoding isoforms 1 and 2 are known in humans. Isoform 1 includes seven TSR (SEQ ID NOs:3-9) and an ADAM-TS spacer (SEQ ID NO:10). Isoform 2 is a truncated version containing TSR 1-4 (SEQ ID NO:3-6) and the ADAM-TS spacer (SEQ ID NO:10). Isoform 2 has a unique 24 amino acid sequence at the C-terminus. The full length isoform 1, GenBank Accession No. NM_019032, encodes a 1074 AA protein, GenBank Accession No. NP_061905, SEQ ID NO:11. The truncated isoform 2, GenBank Accession No. NM_025008, encodes an 877 AA protein, GenBank Accession No. NP_079284, SEQ ID NO:12. Isoforms 1 and 2 have calculated molecular weights of 116415 and 95001 Da, respectively. Mouse ADAMTSL4 also has an isoform, GenBank Accession No. BC016215. The 4.4 kb mouse ADAMTSL4 transcript is expressed in a wide range of fetal and adult tissues[1].

Specific binding sites contained in the thrombospondin type 1 repeat include WSXW, a heparin binding motif, CSVTCG, a CD36, binding motif, and GGWSH, a fibronectin and TGF-β binding motif[1]. The mouse ADAMTSL4 protein is widely expressed in the brain, spinal cord, skin, muscle, liver, lung, spleen and heart, etc.[1].

C. Identification of ADAMTSL4 as a Cancer Gene

Cancer genes (oncogenes and tumor suppressor genes) were defined in a high throughput manner by using proviral tagging. Although viruses have not yet been implicated as a major cause of cancers in humans, research using tumor viruses has led to the discovery of many oncogenes and protooncogenes. In proviral tagging, mice are infected with a retrovirus that does not contain an oncogene (e.g., murine leukemia virus, MLV or murine mammary tumor virus, MMTV)[2-6]. Recently, the host range of this approach has been broadened by the use of a transposon[7, 8].

Figure 1:
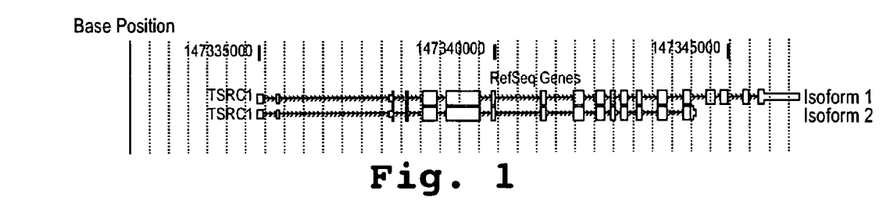
FIG. 1 shows the genomic organization of the human ADAMTSL4 gene on chromosome 1. The structures of isoform 1 and isoform 2 are indicated.
Figure 2:
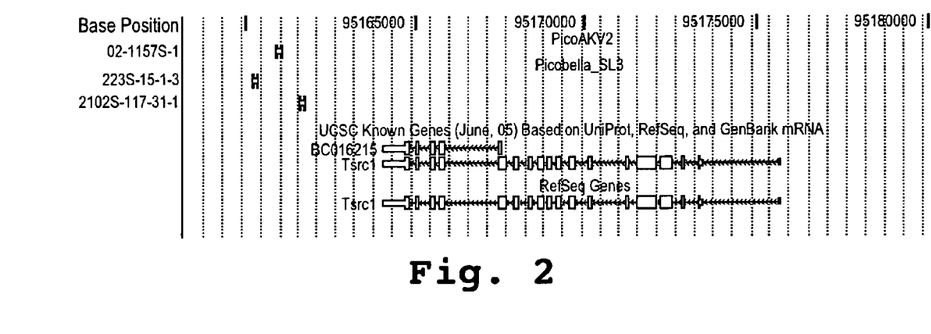
FIG. 2 shows the genomic organization of the mouse ADAMTSL4 locus, as viewed by a customized screen print of the UCSC genome web site browser (March 2005 version of the mm6 gene assembly). Top, base position on chromosome 3. The vertical handlebars represent the retroviral insertions into the locus found in three independent tumors.

During retroviral infection, the virus integrates into the cellular genome and inserts its DNA near or within genes, which leads to various outcomes: (i) the insertion site is too far away from a protooncogene and thus does not activate it. In this case, there will be no selection for that cell. (ii) The provirus inserts within 200 kb of a protooncogene, but not within the gene (type 1). Here, either the viral promoter or the viral enhancer increases the expression level of the protooncogene. (iii) The provirus inserts within a gene, destroying or altering its function (type 2). There will be no selection for a cell that contains either type 1 or type 2 insertion events in a gene that is not a protooncogene or tumor suppressor gene. If integration results in the formation of a tumor, genes adjacent to the integration site can be identified, and classified as either protooncogenes or tumor suppressor genes. This method has been used to identify many new protooncogenes as well as to confirm already known protooncogenes discovered by virtue of their homology to viral oncogenes[2, 3, 5, 6]. A tumor suppressor may be scored if a retrovirus lands within a gene and truncates or destroys it. In these cases, the suppressor may be haplo-insufficient, or alternatively, the mutation on the other allele is provided spontaneously by the mouse. The integration event may also lead to more complex consequences, such as a dominant negative effect of the truncated gene product or the transcription of anti-sense or microRNA. In a screen with T lymphotropic virus SL3-3, two independent tumors were recovered that contained proviral integrations within 5 kb of the 3' end of the ADAMTSL4 gene (FIG. 2, handlebars at base positions 223S-15-1-3 and 2102S-117-31-1). In a second screen with B lymphotropic virus Akv1-99, one tumor was recovered that also contained a proviral integration in the same region, 5 kb of the 3' end of the ADAMTSL4 gene (FIG. 2, handlebar at base position 02-1157S-1). These integrations affect the transcription of the canonical ADAMTSL4 gene and of the truncated form, as present in the transcript for the mouse ADAMTS-like 4 mRNA (GenBank Accession No. BC016215), which may represent a functionally different version of ADAMTSL4.

D. Expression of ADAMTSL4 in Human Tumors and in Normal Tissue

Figure 3A:
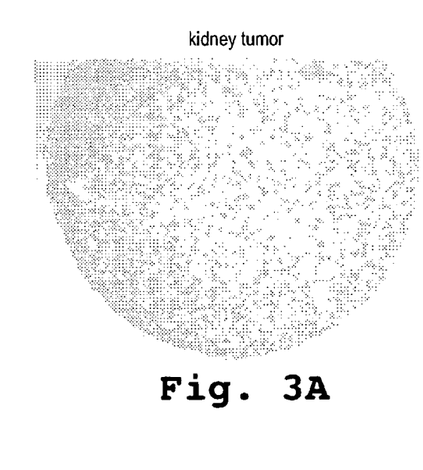
FIG. 3 shows an example of immunohistochemical stains of human kidney tumor (renal cell carcinoma) (left), and matched normal tissue from the same patient (right). The polyclonal rabbit antibody serum used reacts to 2 epitopes: PPQLRPSRKRPCNSQP (amino acid residues 1009 to 1024, SEQ ID NO:1), encoded by exon 16; this epitope is found only in isoform 1, (GenBank Accession No. NP_061905) and SRESGEELDERSCAAGAR (amino acid residues 693 to 710; SEQ ID NO:2), encoded by exon 11; this epitope is found in both isoforms 1 (GenBank Accession No. NP_061905, SEQ ID NO: 11) and 2 (GenBank Accession No. NP_079284, SEQ ID NO:12).
Figure 3B:
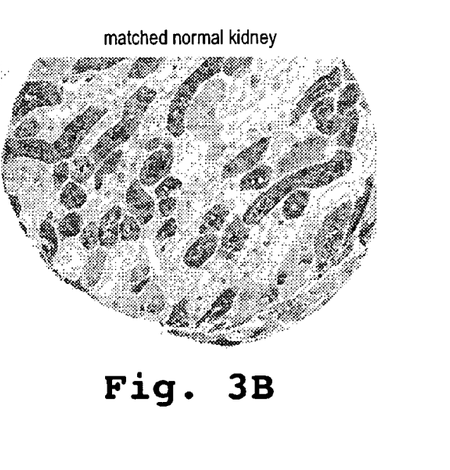

The mutations identified as causal in mouse tumor formation affected both transcripts of the mouse. ADAMTSL4 protein expresses in a wide variety of normal human tissues (www.t1dbase.org) including the brain, ovaries, placenta, spinal cord, testis, and thalamus. Additionally, ADAMTSL4 was found to be strongly expressed in kidney and colon cells. However, the antigenic epitopes to the ADAMTSL4 antibody were missing in colorectal carcinoma and in tumors of the kidney (FIG. 3), whereas the normal counterpart of these tumor cells strongly expressed the ADAMTSL4 protein (FIG. 3). Clearly, the absence of part or all of these epitopes is a marker for these tumors.

More generally, the invention provides a histological method for examining tissue that normally expressed ADAMTSL4 for the presence and extent of cancer. The method is especially useful for examining kidney, colon, and/or rectal tissue. In the method directed to examining kidney tissue, kidney tissue is stained with a labeled antibody specific against a selected domain or epitope of ADAMTSL4, e.g., fluorescence-labeled antibody (see Section E below), to attach the marker to the surface of tissue cells. The presence and extent of kidney cancer in the tissue is then determined based on a reduced distribution and extent of detectable marker with respect to the distribution and extent of marker in normal kidney cells. It will be appreciated that a similar method may be used for other tissues including colorectal tissue.

E. Preparation of Anti-ADAMTSL4 Antibody

This section describes production of anti-ADAMTSL4 antibodies useful for diagnostic and therapeutic purposes, as described further in the sections below. The anti-ADAMTSL4 antibody used in the present invention can be obtained by any variety of conventional methods to produce a monoclonal, polyclonal, and/or recombinant antibody. One preferred antibody, particularly for diagnostic use, is a mouse monoclonal antibody, prepared according to well-known hybridoma methodology. Briefly, human ADAMTSL4 may be first obtained, for example, by expressing the ADAMTSL4 gene. The purified ADAMTSL4 protein acts as an immunogen. Alternatively, a partial peptide of ADAMTSL4 can be used as a sensitization antigen. In particular, for generating antibodies specific against a selected epitope or domain of ADAMTSL4, a peptide defining that domain or epitope may be used as the immunogen. These peptides can be defined by the sequences given in the Sequence Listing below. For example, to generate an antibody specific against an epitope contained in SEQ ID NO:1, the peptide defined by this sequence is employed as the immunogen.

Anti-ADAMTSL4 antibodies useful in diagnostic applications may be labeled with a variety of detectable labels, including detectable reporters, such as enzymes for enzyme-linked immunosorbent assays (ELISA), detectable particles, such as gold particles and reporter-carrying liposomes, colorimetric or fluorescent reporters, labels such as quantum dot nanocrystal particles, radiolabels, and labels such as a biotin label by which secondary detectable labels, such as a reporter-labeled streptavidin label can be attached. In some assay formats, an unlabeled anti-ADAMTSL4 antibody, for example, a mouse IgG antibody, is detected by reaction with a labeled antibody, e.g., a labeled anti-mouse IgG antibody.

For therapeutic uses, human monoclonal antibodies having binding activity to ADAMTSL4 can be produced by sensitizing in vitro human lymphocytes with ADAMTSL4, and causing the sensitized lymphocytes to fuse with the human-derived myeloma cells having a permanent division potential. Alternatively, ADAMTSL4 as an antigen can be administered to a transgenic animal having all the repertories of a human antibody gene to obtain anti-ADAMTSL4 antibody-producing cells, and then human antibodies for ADAMTSL4 may be obtained from the immortalized anti-ADAMTSL4 antibody-producing cells.

In still other methods, human or humanized antibodies specific against ADAMTSL4 antigen can be prepared by recombinant techniques, such as have been reported (see, for example, U.S. Pat. Nos. 6,090,382 and 6,258,562).

F. Diagnostic Methods and Reagents

In one aspect, the invention includes a method of screening for kidney and/or colorectal cancer in a human subject. In another aspect, the invention includes a method of staging treatment of kidney and/or colorectal cancer in a subject. This is done, in accordance with the invention, by reacting a body-fluid sample from the subject with an antibody specific against a selected domain or epitope of ADAMTSL4, and determining from the presence and/or amount of immunoassay product, whether the subject has a reduced level of ADAMTSL4 protein lacking the specific domain or epitope, when compared with a normal range of ADAMTSL4 in human samples. Reduced levels are an indicator of kidney or colorectal cancer.

Preferred body-fluid samples are blood and urine. Where urine is assayed, the assayed level of ADAMTSL4 indicative of kidney or colorectal cancer is typically in the range of less than about 0.1 ng/ml sample fluid.

The assay may be carried out by any of a variety of assay methods used for detecting body-fluid antigens, including ELISA techniques, homogeneous assays, for example, involving fluorescence quenching, and a variety of solid-phase sandwich assays in which the ADAMTSL4 antigen is captured by an anti-ADAMTSL4 antibody carried on a solid support, and the immobilized antigen-antibody complex is labeled with a second anti-ADAMTSL4 antibody, e.g., a second antibody carrying a calorimetric or gold-particle reporter.

Figure 4A:
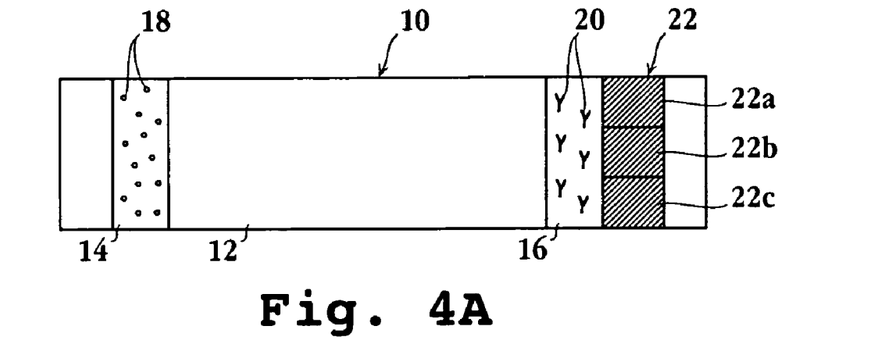
FIGS. 4A and 4B show a solid-phase diagnostic device for determining CELSR1 levels in a human patient, at initial (4A) and final stages (4B) of the assay.
Figure 4B:
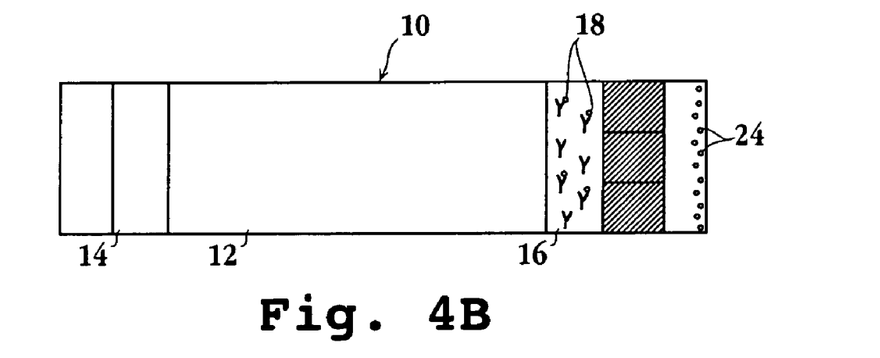

FIGS. 4A and 4B illustrate a solid-phase assay strip constructed in accordance with an embodiment of the invention, suitable for carrying out a sandwich immunoassay of the type just mentioned, and shown in initial and final assay states, respectively. The strip, indicated generally at 10, includes a porous support or pad 12 having a sample-application zone 14 in an upstream region of the support and a sample-detection zone 16 in a downstream region. The sample-application zone includes a detectable anti-ADAMTSL4 antibody reagent, e.g., anti-ADAMTSL4 antibodies labeled with gold particles, and carried in the zone in an unbound, i.e., non-immobilized form. This reagent is indicated by solid circles, such as at 18. Anti-ADAMTSL4 antibodies, which may be the same or different from those in the labeled antibody reagent, are immobilized to the solid support within the detection zone, and are indicated by the "Y" shapes, such as at 20.

Also shown is a reference zone 22 which is located adjacent the detection zone and has one or more colored or shaded regions corresponding to different assay levels of ADAMTSL4 in a body-fluid sample. In the embodiment shown, zone 22 includes three regions 22a, 22b, and 22c, corresponding to an assayed level of ADAMTSL4 (a) below that associated with cancer, (b) corresponding to a lower threshold level associated with cancer, and (c) a level that is substantially higher, e.g., 2-3 times, higher than the threshold layer in region 22b, respectively. These three regions provide a known standard indicator against which the level of detectable reaction produced can be assessed as a level associated with kidney or colorectal cancer. Together, the assay strip and reference zone constitute an assay device for use in screening for kidney and/or colorectal cancer in a human subject, or for staging treatment of kidney and/or colorectal cancer in a human subject.

In operation, a known volume of a body-fluid sample to be tested is added to the sample-application zone of the strip, where it diffuses into the zone, allowing the antibody reagent to react with ADAMTSL4 antigen in the sample to form an antigen-antibody complex. This complex and unbound antibody reagent then migrate downstream by capillarity toward the detection zone, where the antigen-antibody complex is captured by the immobilize antibody and the unbound reagent is carried to the end of the support, as indicated at 24. As can be appreciated, the higher the concentration of antigen in the body fluid, the higher the density of captured reagent in the detection zone and the greater the color or intensity in this zone. This color or intensity produced in the detection zone is compared with the standards in the reference zone to determine a qualitative level of ADAMTSL4 associated with the presence or absence of kidney or colorectal cancer. If a sub-threshold level or threshold level of ADAMTSL4 is observed in the assay, the subject can be classified in a higher-probability category for the presence of cancer and the subject may be recommended for additional testing and/or more frequent testing.

In another embodiment, the assay device includes an assay strip like that described above, but where the known-reference indicator is provided by a strip-reader instrument reader having (i) a reader slot for receiving the assay strip, (ii) a light source and an optical detection, e.g., a spectrophotometric detector, for detecting an assay-related optical condition at the detection zone of the assay strip, (iii) an electronics or processor unit which records and processes a signal from the optical detector, and converts the signal to an assayed level of ADAMTSL4, and (iv) a user display screen or window. The instrument may report the actual ADAMTSL4 body-fluid sample detected, allowing the operator to compare the displayed value with known standard indicator levels provided with the assay strip or instrument, to assess whether the subject has a reduced ADAMTSL4 level associated with kidney cancer and/or colorectal cancer, or to assess the possible stage of the cancer, for purposes of treatment design. Alternatively, the instrument itself may contain stored known-standard indicator levels which can be compared internally with an assayed level to generate an output that indicates whether an reduced ADAMTSL4 level associated with kidney or colorectal cancer has been detected, or to indicate the stage of the cancer.

G. Identifying Genetic Mutation Associated with Cancer

In another aspect, the invention provides a method for identifying mutations associated with increased risk of cancer, such as kidney and/or colorectal cancer, in a human subject. The section below is described in relation to kidney cancer; however, it will be appreciated that the method may be practiced for other cancers involving decreased expression of ADAMTSL4 such as colorectal cancer. In practicing the method, genomic DNA is extracted from human patients having kidney cancer, preferably including patients from men or women representing different racial and age groups. The DNA sequences that are examined, in particular; are (i) one or more of exons 1 to 17 of the ADAMTSL4 on chromosome 1q21, including adjacent splice site acceptor and donor sequences of the exons, (ii) a 5' UTR region within 10 kB or less of exon 1 of the gene, and (iii) a 3' UTR region within 10 kB or less of exon 17.

Mutations at one or more sites along the region are identified by comparing each of the sequences with sequences from the same region derived from normal (wildtype) kidney tissue. Preferably sequences from a number of wildtype individuals are determined to ensure a true wildtype sequence. For each extracted DNA, the patient and wildtype sequences are compared to identify mutations in the patient sequences, and thus mutations that are likely associated with increased risk of kidney cancer.

Once a large number of these mutations are identified, e.g., at least 50-200 or more, they may be used in constructing a genetic screening device, e.g., a gene chip, useful for screening individuals for genetic predisposition to kidney cancer. In one embodiment, the device includes a gene chip, such as shown at 30 in FIG. 5, having an array of regions, such as regions 34, 36, each containing bound known-sequence fragments, such as fragment 37 in region 34. The fragments or probes are preferably 25-70 bases in lengths, and each includes one of the above-identified mutations upstream of the ADAMTSL4 gene that is associated with kidney cancer. Gene-chip construction and detection of mutant sequences with such chips are well known.

Figure 5:
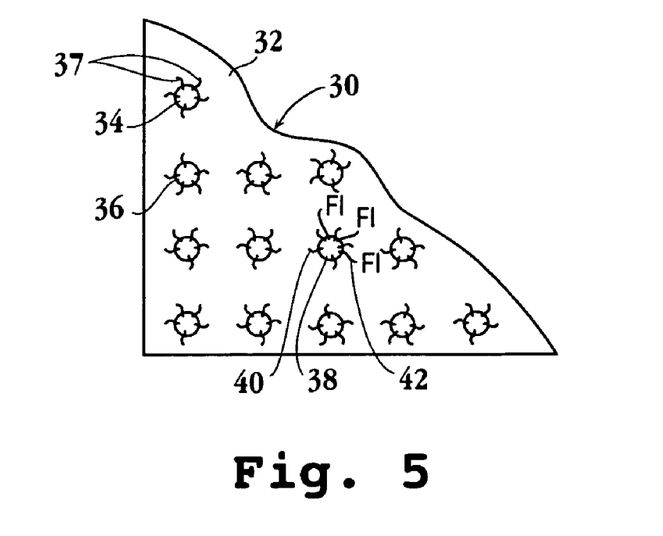
FIG. 5 shows a portion of a gene chip useful for diagnosing genetic predisposition to kidney cancer, constructed in accordance with the present invention.

In a typical genetic-screening procedure, patient cells are obtained, genomic DNA is extracted, and sequence regions of interest are amplified by standard PCR, employing fluoresceinated probes. The amplified material is then reacted with the chip-array sequences, under suitable hybridization conditions, and the array surface is washed to remove unbound material, and then scanned with a suitable chip reader to identify any mutated sequences associated with kidney cancer. The figure shows binding of a labeled genomic DNA fragment, indicated at 42, to an array region 38 having bound probe molecules 40. Detection of a fluorescent signal in this array region is diagnostic of a known genetic mutation in the critical upstream ADAMTSL4 region may be diagnostic of a genetic predisposition to kidney cancer.

In an alternative embodiment, the mutations identified as above are used to construct a set of molecular inversion probes (MIPs) capable of identifying the presence of genomic mutations. The construction and use of MIPs for identifying genetic mutations have been described (see, for example, Wang, et al., *Nucleic Acids Research*, (England) 2005, Vol. 33, p. 21).

H. Treatment Methods and Pharmaceutical Preparations

The invention also includes methods for treating, e.g., reducing the tumor burden in a human subject with a cancer characterized by a reduced expression of ADAMTSL4 in the cancer cells. The section below is described in relation to kidney cancer; however, it will be appreciated that the method may be practiced for other cancers involving decreased expression of ADAMTSL4 such as colorectal cancer.

In one general immunotherapy approach, a patient diagnosed with kidney cancer is first confirmed as having reduced levels of ADAMTSL4, according to assay methods described above. If the subject tests positive in this assay, he is treated by administration of anti-ADAMTSL4 antibody. Preferably the antibody is a human or humanized antibody, prepared as described above, and is administered by IV or subcutaneous injection in a suitable physiological carrier. The antibody dose is preferably 1 to 10 mg/injection, and the patient is treated at intervals of every 14 days or so. During treatment, the patient is monitored for change in status of the cancer, typically by a combination of a tumor-visualization procedure and levels of kidney-related antigens, as above. The treatment may also be carried out in combination with other kidney-cancer treatments, including drug or radioisotope therapy, and may be continued until a desired diminution in tumor size is observed.

While the invention has been described with respect to particular embodiments and applications, it will be appreciated that various changes and modification may be made without departing from the invention as claimed.

Sequences:

SEQ ID NO: 1: Antibody epitope sequence
(residues 1009 to 1024 of isoform 1)
PPQLRPSRKRPCNSQP SEQ ID NO: 2: Antibody epitope sequence
(residues 693-710 of isoform 1 and 2)
SRESGEELDERSCAAGAR SEQ ID NO: 3: Human Thrombospondin Repeat 1 (TSR1) from isoform 1
(residues 47-102)
WGPWVQWASCSQPCGVGVQRRSRTCQLPTVQLHPSLPLPPRPPRHPEALL
PRGQGP SEQ ID NO: 4: Human Thrombospondin Repeat 2 (TSR2) from isoform 1
(residues 668-724)
WKRVGHSACSASCGKGVWRPIFLCISRESGEELDERSCAAGARPPASPEP
CHGTPCP SEQ ID NO: 5: Human Thrombospondin Repeat 3 (TSR3) from isoform 1
(residues 726-784)
YWEAGEWTSCSRSCGPGTQHRQLQCRQEFGGGGSSVPPERCGHLPRPNIT
QSCQLRLCG SEQ ID NO: 6: Human Thrombospondin Repeat 4 (TSR4) from isoform 1
(residues 786-842)
WEVGSPWSQCSVRCGRGQRSRQVRCVGNNGDEVSEQECASGPPQPPSREA
CDMGPCT SEQ ID NO: 7: Human Thrombospondin Repeat 5 (TSR5) from isoform 1
(residues 847-909)
HSDWSSKCSAECGTGIQRRSVVCLGSGAALGPGQGEAGAGTGQSCPTGSR
PPDMRACSLGPCE SEQ ID NO: 8: Human Thrombospondin Repeat 6 (TSR6) from isoform 1
(residues 914-971)
WYTGPWGECSSECGSGTQRRDIICVSKLGTEFNVTSPSNCSHLPRPPALQ
PCQGQACQ -continued Sequences:

SEQ ID NO: 9: Human Thrombospondin Repeat 7 (TSR7) from isoform 1
(residues 973-1026)
RWFSTPWSPCSRSCQGGTQTREVQCLSTNQTLSTRCPPQLRPSRKRPCNS
QPCS SEQ ID NO: 10: Human ADAM-TS Spacer from isoform 1
(residues 485-599)
RLVSGNLTDRGGPLGYQKILWIPAGALRLQIAQLRPSSNYLALRGPGGRS
IINGNWAVDPPGSYRAGGTVFRYNRPPREEGKGESLSAEGPTTQPVDVYM
IFQEENPGVFYQYVI SEQ ID NO: 11: Human thrombospondin repeat containing 1, isoform 1
(GenBank Accession No. NP_061905)
MENWTGRPWLYLLLLLSLPQLCLDQEVLSGHSLQTPTEEGQGPEGVWGPW
VQWASCSQPCGVGVQRRSRTCQLPTVQLHPSLPLPPRPPRHPEALLPRGQ
GPRPQTSPETLPLYRTQSRGRGGPLRGPASHLGREETQEIRAARRSRLRD
PIKPGMFGYGRVPFALPLHRNRRHPRSPPRSELSLISSRGEEAIPSPTPR
AEPPFSANGSPQTELPPTELSVHTPSPQAEPLSPETAQTEVAPRTRPAPLR
HHPRAQASGTEPPSPTHSLGEGGFFRASPQPRRPSSQGWASPQVAGRRPD
PFPSVPRGRGQQGQGPWGTGGTPHGPRLEPDPQHPGAWLPLLSNGPHASS
LWSLFAPSSPIPRCSGESEQLRACSQAPCPPEQPDPRALQCAAFNSQEFM
GQLYQWEPFTEVQGSQRCELNCRPRGFRFYVRHTEKVQDGTLCQPGAPDI
CVAGRCLSPGCDGILGSGRRPDGCGVCGGDDSTCRLVSGNLTDRGGPLGY
QKILWIPAGALRLQIAQLRPSSNYLALRGPGGRSIINGNWAVDPPGSYRA
GGTVFRYNRPPREEGKGESLSAEGPTTQPVDVYMIFQEENPGVFYQYVIS
SPPPILENPTPEPPVPQLQPEILRVEPPLAPAPRPARTPGTLQRQVRIPQ
MPAPPHPRTPLGSPAAYWKRVGHSACSASCGKGVWRPIFLCISRESGEEL
DERSCAAGARPPASPEPCHGTPCPPYWEAGEWTSCSRSCGPGTQHRQLQC
RQEFGGGGSSVPPERCGHLPRPNITQSCQLRLCGHWEVGSPWSQCSVRCG
RGQRSRQVRCVGNNGDEVSEQECASGPPQPPSREACDMGPCTTAWFHSDW
SSKCSAECGTGIQRRSWCLGSGAALGPGQGEAGAGTGQSCPTGSRPPDMR
ACSLGPOERTWRWYTGPWGECSSECGSGTQRRDIICVSKLGTEFNVTSPS
NCSHLPRPPALQPCQGQACQDRWFSTPWSPCSRSCQGGTQTREVQOLSTN
QTLSTRCPPQLRPSRKRPCNSQPOSQRPDDQCKDSSPHCPLWQARLCVYP
YYTATCCRSCAHVLERSPQDPS SEQ ID NO: 12: Human thrombospondin repeat containing 1, isoform 2
(GenBank Accession No. NP_079284)
MENWTGRPWLYLLLLLSLPQLCLDQEVLSGHSLQTPTEEGQGPEGVWGPW
VQWASCSQPCGVGVQRRSRTCQLPTVQLHPSLPLPPRPPRHPEALLPRGQ
GPRPQTSPETLPLYRTQSRGGGPLRGPASHLGREETQEIRAARRSRLRD
PIKPGMFGYGRVPFALPLHRNRRHPRSPPRSELSLISSRGEEAIPSPTPR
AEPPFSANGSPQTELPPTELSVHTPSPQAEPLSPETAQTEVAPRTRPAPLR
HHPRAQASGTEPPSPTHSLGEGGFFRASPQPRRPSSQGWASPQVAGRRPD
PFPSVPRGRGQQGQGPWGTGGTPHGPRLEPDPQHPGAWLPLLSNGPHASS
LWSLFAPSSPIPRCSGESEQLRACSQAPCPPEQPDPRALQCAAFNSQEFM
GQLYQWEPFTEVQGSQRCELNCRPRGFRFYVRHTEKVQDGTLCQPGAPDI
CVAGRCLSPGCDGILGSGRRPDGCGVCGGDDSTCRLVSGNLTDRGGPLGY
QKILWIPAGALRLQIAQLRPSSNYLALRGPGGRSIINGNWAVDPPGSYRA
GGTVFRYNRPPREEGKGESLSAEGPTTQPVDVYMIFQEENPGVFYQYVIS
SPPPILENPTPEPPVPQLQPEILRVEPPLAPAPRPARTPGTLQRQVRIPQ
MPAPPHPRTPLGSPAAYWKRVGHSACSASCGKGVWRPIFLCISRESGEEL
DERSCAAGARPPASPEPCHGTPCPPYWEAGEWTSCSRSCGPGTQHRQLQC
RQEFGGGGSSVPPERCGHLPRPNITQSCQLRLCGHWEVGSPWSQCSVRCG
RGQRSRQVRCVGNNGDEVSEQECASGPPQPPSREACDMGPCTTAWFHSDW
SSKVSPEPPAISCILGNHAQDTSAFPA

It is claimed:

1. A histological method for the diagnosis of the presence of a kidney cancer in a subject, comprising:
   contacting a human kidney tissue sample with an antibody which specifically binds to ADAMTSL4, and
   determining distribution and extent of bound antibody in the tissue sample relative to distribution and extent of bound antibody in a normal kidney tissue, wherein reduced distribution and extent of bound antibody in the kidney tissue sample is indicative of the presence of the cancer.

2. The method of claim 1, wherein the antibody is labeled with a detectable marker.

3. The method of claim 1, wherein the antibody is detected with a second antibody labeled with a detectable marker.

4. The method of claim 1, wherein the human tissue sample is selected from the group consisting of kidney tissue, colon tissue, and rectal tissue.

5. The method of claim 1, wherein the antibody specifically binds an epitope represented by the amino acid sequence selected from the group consisting of SEQ ID NO:1 and SEQ ID NO:2.

6. The method of claim 1, wherein the antibody specifically binds a thrombospondin repeat domain or an ADAM-TS spacer domain.

7. The method of claim 6, wherein the antibody specifically binds the thrombospondin repeat selected from the group consisting of SEQ ID NOS:3-9.

8. The method of claim 6, wherein the antibody specifically binds the ADAM-TS spacer represented by SEQ ID NO:10.

9. The method of claim 1, wherein the antibody is a polyclonal antibody.

10. The method of claim 1, wherein the antibody is a monoclonal antibody.

* * * * *

SEQUENCE LISTING

<160> NUMBER OF SEQ ID NOS: 12

<210> SEQ ID NO 1
<211> LENGTH: 16
<212> TYPE: PRT
<213> ORGANISM: Homo sapiens

```
<400> SEQUENCE: 1

Pro Pro Gln Leu Arg Pro Ser Arg Lys Arg Pro Cys Asn Ser Gln Pro
1               5                   10                  15

<210> SEQ ID NO 2
<211> LENGTH: 18
<212> TYPE: PRT
<213> ORGANISM: Homo sapiens

<400> SEQUENCE: 2

Ser Arg Glu Ser Gly Glu Glu Leu Asp Glu Arg Ser Cys Ala Ala Gly
1               5                   10                  15

Ala Arg

<210> SEQ ID NO 3
<211> LENGTH: 56
<212> TYPE: PRT
<213> ORGANISM: Homo sapiens

<400> SEQUENCE: 3

Trp Gly Pro Trp Val Gln Trp Ala Ser Cys Ser Gln Pro Cys Gly Val
1               5                   10                  15

Gly Val Gln Arg Arg Ser Arg Thr Cys Gln Leu Pro Thr Val Gln Leu
            20                  25                  30

His Pro Ser Leu Pro Leu Pro Arg Pro Pro Arg His Pro Glu Ala
        35                  40                  45

Leu Leu Pro Arg Gly Gln Gly Pro
    50                  55

<210> SEQ ID NO 4
<211> LENGTH: 57
<212> TYPE: PRT
<213> ORGANISM: Homo sapiens

<400> SEQUENCE: 4

Trp Lys Arg Val Gly His Ser Ala Cys Ser Ala Ser Cys Gly Lys Gly
1               5                   10                  15

Val Trp Arg Pro Ile Phe Leu Cys Ile Ser Arg Glu Ser Gly Glu Glu
            20                  25                  30

Leu Asp Glu Arg Ser Cys Ala Ala Gly Ala Arg Pro Pro Ala Ser Pro
        35                  40                  45

Glu Pro Cys His Gly Thr Pro Cys Pro
    50                  55

<210> SEQ ID NO 5
<211> LENGTH: 59
<212> TYPE: PRT
<213> ORGANISM: Homo sapiens

<400> SEQUENCE: 5

Tyr Trp Glu Ala Gly Glu Trp Thr Ser Cys Ser Arg Ser Cys Gly Pro
1               5                   10                  15

Gly Thr Gln His Arg Gln Leu Gln Cys Arg Gln Glu Phe Gly Gly Gly
            20                  25                  30

Gly Ser Ser Val Pro Pro Glu Arg Cys Gly His Leu Pro Arg Pro Asn
        35                  40                  45

Ile Thr Gln Ser Cys Gln Leu Arg Leu Cys Gly
    50                  55
```

<210> SEQ ID NO 6
<211> LENGTH: 57
<212> TYPE: PRT
<213> ORGANISM: Homo sapiens

<400> SEQUENCE: 6

Trp Glu Val Gly Ser Pro Trp Ser Gln Cys Ser Val Arg Cys Gly Arg
1               5                   10                  15

Gly Gln Arg Ser Arg Gln Val Arg Cys Val Gly Asn Asn Gly Asp Glu
            20                  25                  30

Val Ser Glu Gln Glu Cys Ala Ser Gly Pro Pro Gln Pro Pro Ser Arg
        35                  40                  45

Glu Ala Cys Asp Met Gly Pro Cys Thr
    50                  55

<210> SEQ ID NO 7
<211> LENGTH: 63
<212> TYPE: PRT
<213> ORGANISM: Homo sapiens

<400> SEQUENCE: 7

His Ser Asp Trp Ser Ser Lys Cys Ser Ala Glu Cys Gly Thr Gly Ile
1               5                   10                  15

Gln Arg Arg Ser Val Val Cys Leu Gly Ser Gly Ala Ala Leu Gly Pro
            20                  25                  30

Gly Gln Gly Glu Ala Gly Ala Gly Thr Gly Gln Ser Cys Pro Thr Gly
        35                  40                  45

Ser Arg Pro Pro Asp Met Arg Ala Cys Ser Leu Gly Pro Cys Glu
    50                  55                  60

<210> SEQ ID NO 8
<211> LENGTH: 58
<212> TYPE: PRT
<213> ORGANISM: Homo sapiens

<400> SEQUENCE: 8

Trp Tyr Thr Gly Pro Trp Gly Glu Cys Ser Ser Glu Cys Gly Ser Gly
1               5                   10                  15

Thr Gln Arg Arg Asp Ile Ile Cys Val Ser Lys Leu Gly Thr Glu Phe
            20                  25                  30

Asn Val Thr Ser Pro Ser Asn Cys Ser His Leu Pro Arg Pro Pro Ala
        35                  40                  45

Leu Gln Pro Cys Gln Gly Gln Ala Cys Gln
    50                  55

<210> SEQ ID NO 9
<211> LENGTH: 54
<212> TYPE: PRT
<213> ORGANISM: Homo sapiens

<400> SEQUENCE: 9

Arg Trp Phe Ser Thr Pro Trp Ser Pro Cys Ser Arg Ser Cys Gln Gly
1               5                   10                  15

Gly Thr Gln Thr Arg Glu Val Cys Leu Ser Thr Asn Gln Thr Leu
            20                  25                  30

Ser Thr Arg Cys Pro Pro Gln Leu Arg Pro Ser Arg Lys Arg Pro Cys
        35                  40                  45

Asn Ser Gln Pro Cys Ser
    50

```
<210> SEQ ID NO 10
<211> LENGTH: 115
<212> TYPE: PRT
<213> ORGANISM: Homo sapiens

<400> SEQUENCE: 10

Arg Leu Val Ser Gly Asn Leu Thr Asp Arg Gly Gly Pro Leu Gly Tyr
  1               5                  10                  15

Gln Lys Ile Leu Trp Ile Pro Ala Gly Ala Leu Arg Leu Gln Ile Ala
             20                  25                  30

Gln Leu Arg Pro Ser Ser Asn Tyr Leu Ala Leu Arg Gly Pro Gly Gly
         35                  40                  45

Arg Ser Ile Ile Asn Gly Asn Trp Ala Val Asp Pro Pro Gly Ser Tyr
 50                  55                  60

Arg Ala Gly Gly Thr Val Phe Arg Tyr Asn Arg Pro Pro Arg Glu Glu
 65                  70                  75                  80

Gly Lys Gly Glu Ser Leu Ser Ala Glu Gly Pro Thr Thr Gln Pro Val
             85                  90                  95

Asp Val Tyr Met Ile Phe Gln Glu Glu Asn Pro Gly Val Phe Tyr Gln
            100                 105                 110

Tyr Val Ile
            115

<210> SEQ ID NO 11
<211> LENGTH: 1074
<212> TYPE: PRT
<213> ORGANISM: Homo sapiens

<400> SEQUENCE: 11

Met Glu Asn Trp Thr Gly Arg Pro Trp Leu Tyr Leu Leu Leu Leu Leu
  1               5                  10                  15

Ser Leu Pro Gln Leu Cys Leu Asp Gln Glu Val Leu Ser Gly His Ser
             20                  25                  30

Leu Gln Thr Pro Thr Glu Glu Gly Gln Gly Pro Glu Gly Val Trp Gly
         35                  40                  45

Pro Trp Val Gln Trp Ala Ser Cys Ser Gln Pro Cys Gly Val Gly Val
 50                  55                  60

Gln Arg Arg Ser Arg Thr Cys Gln Leu Pro Thr Val Gln Leu His Pro
 65                  70                  75                  80

Ser Leu Pro Leu Pro Pro Arg Pro Pro Arg His Pro Glu Ala Leu Leu
             85                  90                  95

Pro Arg Gly Gln Gly Pro Arg Pro Gln Thr Ser Pro Glu Thr Leu Pro
            100                 105                 110

Leu Tyr Arg Thr Gln Ser Arg Gly Arg Gly Pro Leu Arg Gly Pro
            115                 120                 125

Ala Ser His Leu Gly Arg Glu Glu Thr Gln Glu Ile Arg Ala Ala Arg
            130                 135                 140

Arg Ser Arg Leu Arg Asp Pro Ile Lys Pro Gly Met Phe Gly Tyr Gly
145                 150                 155                 160

Arg Val Pro Phe Ala Leu Pro Leu His Arg Asn Arg Arg His Pro Arg
                165                 170                 175

Ser Pro Pro Arg Ser Glu Leu Ser Leu Ile Ser Ser Arg Gly Glu Glu
            180                 185                 190

Ala Ile Pro Ser Pro Thr Pro Arg Ala Glu Pro Phe Ser Ala Asn Gly
            195                 200                 205
```

-continued

```
Ser Pro Gln Thr Glu Leu Pro Pro Thr Glu Leu Ser Val His Thr Pro
210                 215                 220

Ser Pro Gln Ala Glu Pro Leu Ser Pro Glu Thr Ala Gln Thr Glu Val
225                 230                 235                 240

Ala Pro Arg Thr Arg Pro Ala Pro Leu Arg His His Pro Arg Ala Gln
                245                 250                 255

Ala Ser Gly Thr Glu Pro Pro Ser Pro Thr His Ser Leu Gly Glu Gly
                260                 265                 270

Gly Phe Phe Arg Ala Ser Pro Gln Pro Arg Arg Pro Ser Ser Gln Gly
            275                 280                 285

Trp Ala Ser Pro Gln Val Ala Gly Arg Arg Pro Asp Pro Phe Pro Ser
290                 295                 300

Val Pro Arg Gly Arg Gly Gln Gln Gly Gln Gly Pro Trp Gly Thr Gly
305                 310                 315                 320

Gly Thr Pro His Gly Pro Arg Leu Glu Pro Asp Pro Gln His Pro Gly
                325                 330                 335

Ala Trp Leu Pro Leu Leu Ser Asn Gly Pro His Ala Ser Ser Leu Trp
                340                 345                 350

Ser Leu Phe Ala Pro Ser Ser Pro Ile Pro Arg Cys Ser Gly Glu Ser
            355                 360                 365

Glu Gln Leu Arg Ala Cys Ser Gln Ala Pro Cys Pro Pro Glu Gln Pro
370                 375                 380

Asp Pro Arg Ala Leu Gln Cys Ala Ala Phe Asn Ser Gln Glu Phe Met
385                 390                 395                 400

Gly Gln Leu Tyr Gln Trp Glu Pro Phe Thr Glu Val Gln Gly Ser Gln
                405                 410                 415

Arg Cys Glu Leu Asn Cys Arg Pro Arg Gly Phe Arg Phe Tyr Val Arg
                420                 425                 430

His Thr Glu Lys Val Gln Asp Gly Thr Leu Cys Gln Pro Gly Ala Pro
            435                 440                 445

Asp Ile Cys Val Ala Gly Arg Cys Leu Ser Pro Gly Cys Asp Gly Ile
            450                 455                 460

Leu Gly Ser Gly Arg Arg Pro Asp Gly Cys Gly Val Cys Gly Gly Asp
465                 470                 475                 480

Asp Ser Thr Cys Arg Leu Val Ser Gly Asn Leu Thr Asp Arg Gly Gly
                485                 490                 495

Pro Leu Gly Tyr Gln Lys Ile Leu Trp Ile Pro Ala Gly Ala Leu Arg
                500                 505                 510

Leu Gln Ile Ala Gln Leu Arg Pro Ser Ser Asn Tyr Leu Ala Leu Arg
            515                 520                 525

Gly Pro Gly Gly Arg Ser Ile Ile Asn Gly Asn Trp Ala Val Asp Pro
            530                 535                 540

Pro Gly Ser Tyr Arg Ala Gly Gly Thr Val Phe Arg Tyr Asn Arg Pro
545                 550                 555                 560

Pro Arg Glu Glu Gly Lys Gly Glu Ser Leu Ser Ala Glu Gly Pro Thr
                565                 570                 575

Thr Gln Pro Val Asp Val Tyr Met Ile Phe Gln Glu Glu Asn Pro Gly
                580                 585                 590

Val Phe Tyr Gln Tyr Val Ile Ser Ser Pro Pro Ile Leu Glu Asn
            595                 600                 605

Pro Thr Pro Glu Pro Pro Val Pro Gln Leu Gln Pro Glu Ile Leu Arg
610                 615                 620
```

-continued

Val Glu Pro Pro Leu Ala Pro Ala Pro Arg Pro Ala Arg Thr Pro Gly
625                 630                 635                 640

Thr Leu Gln Arg Gln Val Arg Ile Pro Gln Met Pro Ala Pro Pro His
        645                 650                 655

Pro Arg Thr Pro Leu Gly Ser Pro Ala Ala Tyr Trp Lys Arg Val Gly
            660                 665                 670

His Ser Ala Cys Ser Ala Ser Cys Gly Lys Gly Val Trp Arg Pro Ile
        675                 680                 685

Phe Leu Cys Ile Ser Arg Glu Ser Gly Glu Glu Leu Asp Glu Arg Ser
    690                 695                 700

Cys Ala Ala Gly Ala Arg Pro Pro Ala Ser Pro Glu Pro Cys His Gly
705                 710                 715                 720

Thr Pro Cys Pro Pro Tyr Trp Glu Ala Gly Glu Trp Thr Ser Cys Ser
            725                 730                 735

Arg Ser Cys Gly Pro Gly Thr Gln His Arg Gln Leu Gln Cys Arg Gln
            740                 745                 750

Glu Phe Gly Gly Gly Gly Ser Val Pro Pro Glu Arg Cys Gly His
        755                 760                 765

Leu Pro Arg Pro Asn Ile Thr Gln Ser Cys Gln Leu Arg Leu Cys Gly
770                 775                 780

His Trp Glu Val Gly Ser Pro Trp Ser Gln Cys Ser Val Arg Cys Gly
785                 790                 795                 800

Arg Gly Gln Arg Ser Arg Gln Val Arg Cys Val Gly Asn Asn Gly Asp
            805                 810                 815

Glu Val Ser Glu Gln Glu Cys Ala Ser Gly Pro Gln Pro Pro Ser
        820                 825                 830

Arg Glu Ala Cys Asp Met Gly Pro Cys Thr Thr Ala Trp Phe His Ser
        835                 840                 845

Asp Trp Ser Ser Lys Cys Ser Ala Glu Cys Gly Thr Gly Ile Gln Arg
    850                 855                 860

Arg Ser Val Val Cys Leu Gly Ser Gly Ala Ala Leu Gly Pro Gly Gln
865                 870                 875                 880

Gly Glu Ala Gly Ala Gly Thr Gly Gln Ser Cys Pro Thr Gly Ser Arg
            885                 890                 895

Pro Pro Asp Met Arg Ala Cys Ser Leu Gly Pro Cys Glu Arg Thr Trp
        900                 905                 910

Arg Trp Tyr Thr Gly Pro Trp Gly Glu Cys Ser Ser Glu Cys Gly Ser
        915                 920                 925

Gly Thr Gln Arg Arg Asp Ile Ile Cys Val Ser Lys Leu Gly Thr Glu
    930                 935                 940

Phe Asn Val Thr Ser Pro Ser Asn Cys Ser His Leu Pro Arg Pro Pro
945                 950                 955                 960

Ala Leu Gln Pro Cys Gln Gly Gln Ala Cys Gln Asp Arg Trp Phe Ser
            965                 970                 975

Thr Pro Trp Ser Pro Cys Ser Arg Ser Cys Gln Gly Gly Thr Gln Thr
        980                 985                 990

Arg Glu Val Gln Cys Leu Ser Thr Asn Gln Thr Leu Ser Thr Arg Cys
    995                 1000                1005

Pro Pro  Gln Leu Arg Pro Ser  Arg Lys Arg Pro Cys  Asn Ser Gln
    1010                1015                1020

Pro Cys  Ser Gln Arg Pro Asp  Asp Gln Cys Lys Asp  Ser Ser Pro
    1025                1030                1035

-continued

```
His Cys Pro Leu Val Val Gln Ala Arg Leu Cys Val Tyr Pro Tyr
    1040                1045                1050

Tyr Thr Ala Thr Cys Cys Arg Ser Cys Ala His Val Leu Glu Arg
    1055                1060                1065

Ser Pro Gln Asp Pro Ser
    1070

<210> SEQ ID NO 12
<211> LENGTH: 877
<212> TYPE: PRT
<213> ORGANISM: Homo sapiens

<400> SEQUENCE: 12

Met Glu Asn Trp Thr Gly Arg Pro Trp Leu Tyr Leu Leu Leu Leu
1               5                   10                  15

Ser Leu Pro Gln Leu Cys Leu Asp Gln Glu Val Leu Ser Gly His Ser
                20                  25                  30

Leu Gln Thr Pro Thr Glu Glu Gly Gln Gly Pro Glu Gly Val Trp Gly
                35                  40                  45

Pro Trp Val Gln Trp Ala Ser Cys Ser Gln Pro Cys Gly Val Gly Val
50                      55                  60

Gln Arg Arg Ser Arg Thr Cys Gln Leu Pro Thr Val Gln Leu His Pro
65                  70                  75                  80

Ser Leu Pro Leu Pro Pro Arg Pro Arg His Pro Glu Ala Leu Leu
                85                  90                  95

Pro Arg Gly Gln Gly Pro Arg Pro Gln Thr Ser Pro Glu Thr Leu Pro
            100                 105                 110

Leu Tyr Arg Thr Gln Ser Arg Gly Arg Gly Pro Leu Arg Gly Pro
            115                 120                 125

Ala Ser His Leu Gly Arg Glu Glu Thr Gln Glu Ile Arg Ala Ala Arg
    130                 135                 140

Arg Ser Arg Leu Arg Asp Pro Ile Lys Pro Gly Met Phe Gly Tyr Gly
145                 150                 155                 160

Arg Val Pro Phe Ala Leu Pro Leu His Arg Asn Arg Arg His Pro Arg
                165                 170                 175

Ser Pro Pro Arg Ser Glu Leu Ser Leu Ile Ser Ser Arg Gly Glu Glu
            180                 185                 190

Ala Ile Pro Ser Pro Thr Pro Arg Ala Glu Pro Phe Ser Ala Asn Gly
        195                 200                 205

Ser Pro Gln Thr Glu Leu Pro Thr Glu Leu Ser Val His Thr Pro
    210                 215                 220

Ser Pro Gln Ala Glu Pro Leu Ser Pro Glu Thr Ala Gln Thr Glu Val
225                 230                 235                 240

Ala Pro Arg Thr Arg Pro Ala Pro Leu Arg His His Pro Arg Ala Gln
                245                 250                 255

Ala Ser Gly Thr Glu Pro Pro Ser Pro Thr His Ser Leu Gly Glu Gly
            260                 265                 270

Gly Phe Phe Arg Ala Ser Pro Gln Pro Arg Arg Pro Ser Ser Gln Gly
        275                 280                 285

Trp Ala Ser Pro Gln Val Ala Gly Arg Arg Pro Asp Pro Phe Pro Ser
    290                 295                 300

Val Pro Arg Gly Arg Gly Gln Gln Gly Gln Gly Pro Trp Gly Thr Gly
305                 310                 315                 320

Gly Thr Pro His Gly Pro Arg Leu Glu Pro Asp Pro Gln His Pro Gly
                325                 330                 335
```

-continued

```
Ala Trp Leu Pro Leu Leu Ser Asn Gly Pro His Ala Ser Ser Leu Trp
            340                 345                 350

Ser Leu Phe Ala Pro Ser Ser Pro Ile Pro Arg Cys Ser Gly Glu Ser
            355                 360                 365

Glu Gln Leu Arg Ala Cys Ser Gln Ala Pro Cys Pro Pro Glu Gln Pro
            370                 375                 380

Asp Pro Arg Ala Leu Gln Cys Ala Ala Phe Asn Ser Gln Glu Phe Met
385                 390                 395                 400

Gly Gln Leu Tyr Gln Trp Glu Pro Phe Thr Glu Val Gln Gly Ser Gln
            405                 410                 415

Arg Cys Glu Leu Asn Cys Arg Pro Arg Gly Phe Arg Phe Tyr Val Arg
            420                 425                 430

His Thr Glu Lys Val Gln Asp Gly Thr Leu Cys Gln Pro Gly Ala Pro
            435                 440                 445

Asp Ile Cys Val Ala Gly Arg Cys Leu Ser Pro Gly Cys Asp Gly Ile
            450                 455                 460

Leu Gly Ser Gly Arg Arg Pro Asp Gly Cys Gly Val Cys Gly Gly Asp
465                 470                 475                 480

Asp Ser Thr Cys Arg Leu Val Ser Gly Asn Leu Thr Asp Arg Gly Gly
            485                 490                 495

Pro Leu Gly Tyr Gln Lys Ile Leu Trp Ile Pro Ala Gly Ala Leu Arg
            500                 505                 510

Leu Gln Ile Ala Gln Leu Arg Pro Ser Ser Asn Tyr Leu Ala Leu Arg
            515                 520                 525

Gly Pro Gly Gly Arg Ser Ile Ile Asn Gly Asn Trp Ala Val Asp Pro
            530                 535                 540

Pro Gly Ser Tyr Arg Ala Gly Gly Thr Val Phe Arg Tyr Asn Arg Pro
545                 550                 555                 560

Pro Arg Glu Glu Gly Lys Gly Glu Ser Leu Ser Ala Glu Gly Pro Thr
            565                 570                 575

Thr Gln Pro Val Asp Val Tyr Met Ile Phe Gln Glu Glu Asn Pro Gly
            580                 585                 590

Val Phe Tyr Gln Tyr Val Ile Ser Ser Pro Pro Ile Leu Glu Asn
            595                 600                 605

Pro Thr Pro Glu Pro Pro Val Pro Gln Leu Gln Pro Glu Ile Leu Arg
            610                 615                 620

Val Glu Pro Pro Leu Ala Pro Ala Pro Arg Pro Ala Arg Thr Pro Gly
625                 630                 635                 640

Thr Leu Gln Arg Gln Val Arg Ile Pro Gln Met Pro Ala Pro Pro His
            645                 650                 655

Pro Arg Thr Pro Leu Gly Ser Pro Ala Ala Tyr Trp Lys Arg Val Gly
            660                 665                 670

His Ser Ala Cys Ser Ala Ser Cys Gly Lys Gly Val Trp Arg Pro Ile
            675                 680                 685

Phe Leu Cys Ile Ser Arg Glu Ser Gly Glu Glu Leu Asp Glu Arg Ser
            690                 695                 700

Cys Ala Ala Gly Ala Arg Pro Pro Ala Ser Pro Glu Pro Cys His Gly
705                 710                 715                 720

Thr Pro Cys Pro Pro Tyr Trp Glu Ala Gly Glu Trp Thr Ser Cys Ser
            725                 730                 735

Arg Ser Cys Gly Pro Gly Thr Gln His Arg Gln Leu Gln Cys Arg Gln
            740                 745                 750
```

```
                                        -continued
Glu Phe Gly Gly Gly Ser Ser Val Pro Pro Glu Arg Cys Gly His
        755             760             765

Leu Pro Arg Pro Asn Ile Thr Gln Ser Cys Gln Leu Arg Leu Cys Gly
    770             775             780

His Trp Glu Val Gly Ser Pro Trp Ser Gln Cys Ser Val Arg Cys Gly
785             790             795                     800

Arg Gly Gln Arg Ser Arg Gln Val Arg Cys Val Gly Asn Asn Gly Asp
                805             810                 815

Glu Val Ser Glu Gln Glu Cys Ala Ser Gly Pro Pro Gln Pro Pro Ser
            820             825             830

Arg Glu Ala Cys Asp Met Gly Pro Cys Thr Thr Ala Trp Phe His Ser
        835             840             845

Asp Trp Ser Ser Lys Val Ser Pro Glu Pro Pro Ala Ile Ser Cys Ile
    850             855             860

Leu Gly Asn His Ala Gln Asp Thr Ser Ala Phe Pro Ala
865             870             875
```